United States Patent [19]

Bleicher

[11] Patent Number: 4,799,487

[45] Date of Patent: Jan. 24, 1989

[54] REANIMATION DEVICE AND METHOD FOR TREATING THE PARALYZED FACE

[76] Inventor: Joel N. Bleicher, R.R. #2, Box 70, Council Bluffs, Iowa 51501

[21] Appl. No.: 48,549

[22] Filed: May 11, 1987

[51] Int. Cl.$^4$ .................. A61N 1/00; H05G 00/00
[52] U.S. Cl. .................................. 128/419 R
[58] Field of Search ............ 128/419 R, 905, 745, 128/733, 793; 623/4, 24, 25

[56] References Cited

U.S. PATENT DOCUMENTS

| | | | |
|---|---|---|---|
| 3,204,637 | 2/1963 | Frank et al. | 128/421 |
| 3,662,758 | 5/1972 | Glover | 128/421 |
| 3,727,616 | 4/1973 | Lenzkes | 128/422 |
| 4,197,840 | 4/1980 | Beck et al. | 128/1.3 |
| 4,390,023 | 6/1983 | Rise | 128/421 |
| 4,524,774 | 6/1985 | Hildebrandt | 128/421 |
| 4,558,704 | 12/1985 | Petrofsky | 128/423 R |
| 4,582,049 | 4/1986 | Ylrisake | 128/421 |
| 4,612,934 | 9/1986 | Borkam | 128/421 |
| 4,642,769 | 2/1987 | Petrofsky | 128/421 |

FOREIGN PATENT DOCUMENTS 2335475 1/1975 Fed. Rep. of Germany ...... 128/421

Primary Examiner—Francis Jaworski
Assistant Examiner—George Manuel
Attorney, Agent, or Firm—E. Robert Newman

[57] ABSTRACT

A device for the re-animation of the paralyzed face including electrodes implanted in muscles on the healthy side of the face, said electrodes sensing contractions and sending signals to a microprocessor, which in turn processes said signals and re-transmits them to other electrodes implanted in the counterpart muscles in the paralyzed side of the face, thereby stimulating said counterpart muscles to contract. Also, a method for treating the paralyzed face in which some exigency requires a delay before said device can be installed, including periodically electronically stimulating the muscles on the paralyzed side of the face, thereby preventing atrophy for whatever time span is required. In another embodiment an electromagnet implanted in the bone below the eye on the paralyzed side of the face receives signals from the non-paralyzed side of the face, which energize a current causing the electromagnet to pull the eyelid shut, said eyelid having ferrous material implanted therein.

12 Claims, 1 Drawing Sheet

REANIMATION DEVICE AND METHOD FOR TREATING THE PARALYZED FACE

FIELD OF THE INVENTION

The present invention relates generally to an apparatus for activating paralyzed facial muscles and more particularly to a device which stimulates muscles on the paralyzed side of the face or stimulates that muscle action upon receiving a signal generated by their counterparts on the healthy side of the face. The present invention relates also to a method for treating a paralyzed face when it is desirable to wait a period of time before applying the device of this invention, such as for a nerve to regenerate.

BACKGROUND ART

Facial paralysis can result from stroke, traumatic injury, or disease. Such injury might occur in an accident or while a patient is undergoing surgery. Whereas any paralysis is undesirable, facial or otherwise, there are certain problems associated with a paralyzed face which are unique. If a person cannot close an eye, eyesight and potentially the eyeball will be lost as a result of dryness caused by exposure. If one side of the mouth is paralyzed, it is not possible to retain food or liquid in the mouth. Depression resulting from the appearance of a paralyzed face can be almost as debilitating for some persons as the loss of an eye or the inability to eat or drink in a normal fashion. Beyond these more obvious problems of facial paralysis, is the loss of the ability to effectively communicate through facial expression (smile, laugh, frown, cry, etc.).

Some prior art devices include gold weights implanted in the upper eyelid, permanent magnets implanted in the upper and lower eyelids, springs, rubber bands, and surgical techniques. While any of the above solutions are preferably to losing an eye or being an alimentary cripple for the rest of one's life, they all fall far short of providing relief anywhere close to approaching a restoration of normal functions.

SUMMARY OF THE INVENTION

It is an object of the present invention to provide an improved device for dealing with the problems of facial paralysis.

Another object of the invention is to provide a device which will cause paralyzed facial muscles to function in a manner which would avoid loss of eyesight, ability to hold food or liquid in the mouth, or unsightly appearance associated with facial paralysis.

Yet another object of the present invention is the provision of a device which will permit muscles on the paralyzed side of a face to involuntarily contract whenever the counterpart muscles on the good side of the face contract, either voluntarily or involuntarily.

A further object of the invention is to provide a method of treatment of a denervated facial muscle which will permit use of the present device after waiting for nerve regeneration and/or other necessary delays, a time lapse during which muscle atrophy might otherwise preclude said use.

Unlike most other parts of the body, facial muscles contract naturally on both sides of the face in unison. As an example, blinking is most often the result of an involuntary contraction of the muscles which control the closing and opening of the eyes. When one blinks voluntarily the signal from the brain is simultaneously sent to the appropriate muscles on both sides of the face. To blink on only one side of the face is a feat which must be learned. We all can remember how difficult it was to close only one eye when we first tried as children. In a general sense, the same may be said for other facial muscles, such as those controlling the opening and closing of the mouth, the jaws, the eyebrows, and the cheeks. The same phenomenon applies to most facial expressions where combinations of various facial muscles are employed voluntarily or involuntarily.

While it is theoretically possible for facial paralysis to occur on both sides of the face, if it ever does it is extremely rare. It is well-known that a muscle produces an increase in electrical potential when it contracts which may be picked up by implanted sensors. It is also well-known that an electric charge will stimulate a muscle to contract. The device of the present invention senses the changes in electrical potential from any contraction of the concerned muscles on the healthy side of the face such as those which cause the eyes to blink, transmits signals reflecting that potential change to a microprocessor which transforms those signals as directed by program (including the shape and amplification thereof) and in turn transmits the processed signals to the affected side of the face where they stimulate the counterpart muscles to contract in a commensurate manner.

The inventor has discovered that the normal rate of atrophy experienced by a denervated muscle upon damage or destruction of a nerve can be substantially retarded through periodic electronic stimulation of that muslce. This new knowledge is applied in a method of treating some cases of facial paralysis which otherwise might not be able to benefit by the device of this invention. In some instances it is necessary for a nerve to regenerate before the instant device can be implanted. During this period of time an unused muscle can atrophy to an extent which would preclude the present device. In such a situation continuous periodic muscle stimulation will substantially halt muscle atrophy while the nerve is regenerating, after which time the instant device can be implanted.

Other exigencies may lead to such treatment. Facial expression and other more complex functions of the facial muscles might result in delay for microprocessor programming, during which time key muscles would atrophy. Treating the unused muscles with such periodic stimulation would adequately deter atrophy and serve to maintain the muscle while such programming is being accomplished. Even the ability to forestall the installation of the device of this invention for the development of anticipated or unknown technology would be a godsend to many sufferers of facial paralysis.

The device as set forth above is not useful in cases of peripheral paralysis. In such instances, where the nerve has been completely destroyed or severed after leaving the skull, the muscle would not contract on stimulus. For cases of peripheral paralysis the action of certain muscles may be simulated through an electromagnet. For example, in another embodiment of the device an electromagnet is implanted in the bone just under the eye on the paralyzed side of the face. Ferrous metal is implanted in the upper eyelid. The signal transmitted when the eye is opened or closed on the healthy side of the face is received by the microprocessor, processed and amplified as needed and then transmitted in the form of electrical current to the electromagnet. Thus, each time the good eye blinks or closes and opens, either involuntarily or voluntarily, the eye on the side of the face which suffers from peripheral paralysis will do the same.

These and other objects, advantages and novel features of the present invention will become apparent from the following detailed description of the invention when considered in conjunction with the accompanying drawings.

DESCRIPTION OF THE BEST MODE

Figure 1:
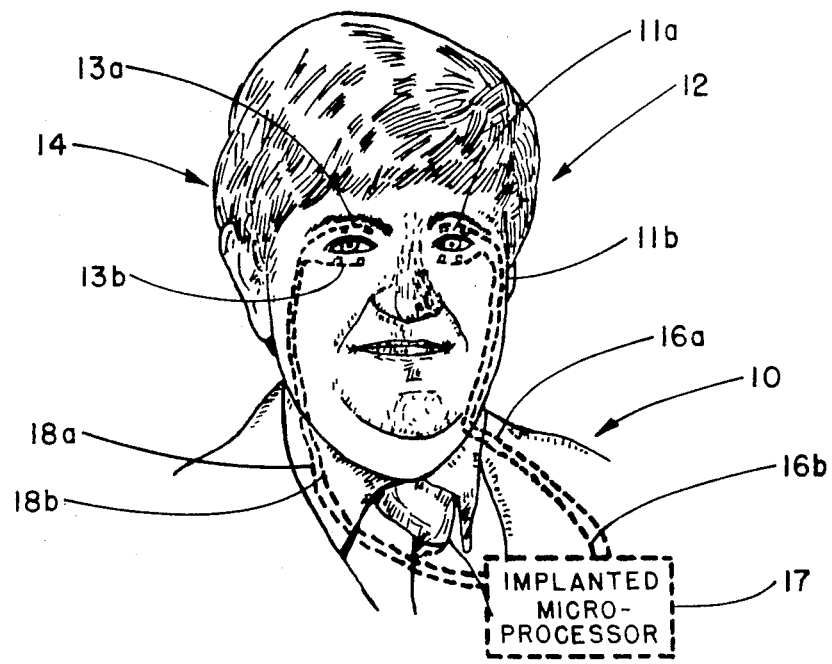
FIG. 1 is a schematic showing of a reanimation device in accordance with the present system mounted on the face of a person whose muscles controlling the opening and closing of the eye on one side are paralyzed.

Referring now to the drawings wherein like reference numerals designate identical or corresponding parts throughout the several views, FIG. 1 shows the device, designated generally at 10, as it would be installed with electrodes implanted on both sides of the face and located so as to service an eye which remains open due to paralysis. Pairs of electrodes 11a and 11b are implanted in the well side, designated generally at 12, of the face in relation to those muscles (not shown) which when contracted close the eye. Likewise, pairs of electrodes 13a and 13b are implanted in the paralyzed side, designated generally at 14, of the face in relation to the counterpart muscles which, if healthy, would cause the eye to close when contracted.

One pair of electrodes 11a is connected by implanted wire pair 16a (schematically indicated in FIG. 1 as a single dashed line) to implanted microprocessor 17. The other pair 11b is connected by implanted wire pair 16b (schematically indicated in FIG. 1 as a single dashed line) to microprocessor 17 in a similar manner. For facial functions requiring more individual muscles additional electrodes and wire pairs would be involved.

Microprocessor 17 receives signals from wire pairs 16a and 16b, amplifies and processes said signals as to amplitude, width, shape, etc. in accordance with the needs of the counterpart muscles on the paralyzed side 14 of the face, through programming techniques known in the prior art. It should be appreciated that other relational arrangements among wires 16a, 16b, and microprocessor 17 are known, the one shown being only a schematic illustration.

Once processed in such manner signals are transmitted from microprocessor 17 through partially implanted wire pairs 18a and 18b, to each pair 13a and 13b of electrodes, respectively, implanted in the paralyzed side 14 of the face.

Once so installed upon a face suffering from paralysis resulting in one eye remaining opening, every time the good eye blinks or is voluntarily closed the other eye will do likewise. It is believed that a signal amplification in an order of magnitude of several thousand times that stimulated by the muscles of the good side 12 of the face is required in this procedure.

Prior art is known which would enable the above-described reanimation device to be transmitted without wire connections. By way of example, reference is made to U.S. Pat. No. 4,524,774 in which implanted muscles potential sensors have a transmitter having power supplied with received high-frequency energy; the implanted stimulus producers have a receiver, a stimulus generator, and their own power supply driven by received high-frequency energy; and a data processing unit has a telemtry receiver and a telemetry transmitter each designed for modulation.

In situations in which it is not possible or desirable to immediately install this device, as set forth hereinabove, electrodes would be first implanted in the paralyzed side of the face and used to periodically stimulate muscle contraction. As has been discovered muscle treated in such manner would not substantially atrophy over whatever period of time is necessary before the remainder of the device could be installed, or further perfected and then installed.

Figure 2:
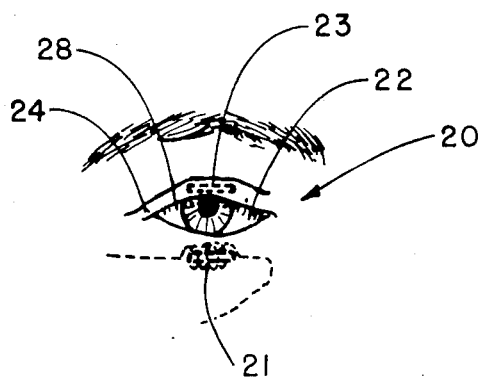
FIG. 2 is a partial schematic showing of another embodiment of the device mounted on the face of a person whose muscles controlling the opening and closing of the eye on one side suffer from peripheral paralysis, showing the eye open.
Figure 3:
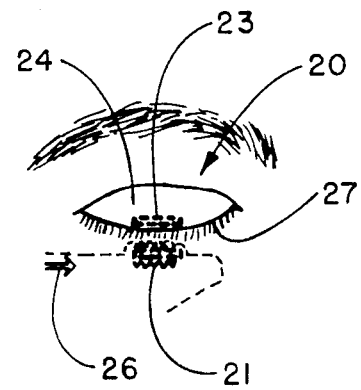
FIG. 3 is a partial schematic showing of another embodiment of the device mounted on the face of a person whose muscles controlling the opening and closing of the eye on one side suffer from peripheral paralysis, showing the eye closed.

Another embodiment of the reanimation device, designated generally at 20, of the present invention is for use in cases of peripheral paralysis; that is, when the nerve leaving the brain has been completely destroyed or severed. Referring to FIGS. 2 and 3; electromagnet 21 is schematically shown as though embedded in the bone just below the eye 22. A small amount of ferrous material 23 is implanted in the upper eyelid 24. The effect of an electric current, indicated by arrow 26, being present in electromagnet 21 is seen in FIG. 3. Ferrous material 23 has pulled eyelid 24 to closed position 27. When current is not present in electromagnet 21 (see FIG. 2) the eye will return to its open position 28 (muscles not contracted).

It will be readily understood that the particular disposition or arrangement or nature of the elements of the invention are not of the essence of the invention, and that many variations, substitutions, and modifications may be made in departure from their particular construction and characterization in the drawings and foregoing description without departing from the true spirit of the invention. It is therefore to be understood that the invention should be limited only by the breadth and scope of the appended claims.

What is claimed is:

1. A re-animation device for a face paralyzed on one side only, comprising:
   means for sensing muscle-stimulation signals from the muscles controlling a specific facial function on the non-paralyzed side of the face, said sensing means being adapted to transmit said signals;
   means for receiving said muscle-stimulation signals, said receiving means being adapted to process said signals as needed by the muscles controlling said specific facial function on the paralyzed side of the face and adapted to transmit said processed signals; and
   means for stimulating said muscles controlling said specific facial function on the paralyzed side of the face, said stimulating means being adapted to receive said processed signals.

2. The re-animation device as set forth in claim 1 wherein said muscle-stimulation signal sensing means is a positive and negative electrode implanted in each of the muscles which control said specific facial function on the non-paralyzed side of the face, said electrodes each being connected to wires for transmitting said signals and wherein said muscle-stimulation signal receiving means is a negative and positive lead to which said wire connected to said positive electrode and said wire connected to said negative electrode are connected, respectively.

3. The re-animation device as set forth in claim 1 wherein said muscle stimulating means is a positive and negative electrode implanted in each of the muscles which control said specific facial function on the paralyzed side of the face, said electrodes each being connected to wires for receiving said signals and wherein said muscle-stimulated signal receiving means has a negative and positive lead to which said wire connected to said positive electrode and said wire connected to said negative electrode are connected, respectively.

4. The re-animation device as set forth in claim 1 wherein said muscle sensing means is a first positive and first negative electrode implanted in each of the muscles which control said specific facial function on the non-paralyzed side of the face, said first positive and first negative electrodes each being connected to wires for transmitting said signals; wherein said muscle stimulating means is a second positive and a second negative electrode implanted in each of the muscles which control said specific facial function on the paralyzed side of the face, said second positive and second negative electrodes each being connected to a wire for receiving said signals; and wherein said muscle-stimulation signal receiving means is a first negative and first positive lead to which said wire connected to said first positive electrode and said wire connected to said first negative electrode are connected, respectively, and has a second negative lead and second positive lead to which said wire connected to said second positive electrode and said wire connected to said second negative electrode are connected, respectively.

5. The re-animation device as set forth in claim 1 wherein said muscle-stimulation signal receiving means includes microprocessor means and amplification means for processing said signals.

6. The re-animation device as set forth in claim 2 wherein said muscle-stimulation signal receiving means includes microprocessor means and amplification means for processing said signals.

7. The re-animation device as set forth in claim 3 wherein said muscle-stimulation signal receiving means includes microprocessor means and amplification means for processing said signals.

8. The re-animation device as set forth in claim 4 wherein said muscle-stimulation signal receiving means includes microprocessor means and amplification means for processing said signals.

9. A method for treating a face paralyzed on one side only, comprising the steps of:
implanting means for electronically stimulating muscles controlling a specific facial function on the paralyzed side of the face;
periodically stimulating said muscles on the paralyzed side of the face for;
implanting means for sensing muscle-stimulation signals from the muscles controlling said specific facial function on the non-paralyzed side of the face, said sensing means being adapted to transmit said signals;
means for receiving said muscle-stimulation signals, said receiving means being adapted to process said signals as needed by the muscles controlling said specific facial function on the paralyzed side of the face and adapted to transmit said processed signals; and
adapting said stimulating means implanted in the paralyzed side of the face to receive said processed signals.

10. A re-animation device for a face having the muscle controlling the opening and closing of the eye paralyzed on one side of the face only, comprising:
electromagnetic means adapted to be implanted in the bone under the eye on the paralyzed side of the face;
ferrous metal means adapted to be implanted in the upper eyelid of the eye on the paralyzed side of the face;
means for transmitting electrical current to said electromagnetic means, said transmitting means being adapted to receive muscle-stimulation signals and adapted to process said signals as needed by said electromagnetic means; and
means for sensing muscle-stimulation signals from the muscles controlling the opening and closing of the eye on the non-paralyzed side of the face, said means being adapted to transmit said signals.

11. The re-animation device as set forth in claim 10 wherein said muscle sensing means is a positive and negative electrode implanted in each of the muscles controlling the opening and closing of the eye on the non-paralyzed side of the face, said electrodes each being connected to wires for transmitting said signals and wherein said electrical current transmitting means has a negative and postive lead to which said wire connected to said positive electrode and said wire connected to said negative electrode are connected, respectively.

12. The re-animation as set forth in claim 11 wherein said electrical current transmission means includes microprocessor means and amplification means for processing said signals.

* * * * *